(12) United States Patent
Werner et al.

(10) Patent No.: US 9,797,891 B2
(45) Date of Patent: Oct. 24, 2017

(54) METHOD AND SYSTEM FOR DETERMINING A BIOLOGICAL RESPONSE OF A TARGET TO A SOLUBLE CANDIDATE SUBSTANCE

(71) Applicant: F. Hoffmann-La Roche AG, Basel (CH)

(72) Inventors: Michael Werner, Basel (CH); Rainer E. Martin, Basel (CH); Remo Anton Hochstrasser, Oberwil (CH)

(73) Assignee: F. Hoffmann-La Roche AG, Basel (CH)

( * ) Notice: Subject to any disclaimer, the term of this patent is extended or adjusted under 35 U.S.C. 154(b) by 232 days.

(21) Appl. No.: 14/771,437

(22) PCT Filed: Mar. 4, 2014

(86) PCT No.: PCT/EP2014/054117
§ 371 (c)(1),
(2) Date: Aug. 28, 2015

(87) PCT Pub. No.: WO2014/135512
PCT Pub. Date: Sep. 12, 2014

(65) Prior Publication Data
US 2016/0011180 A1    Jan. 14, 2016

(30) Foreign Application Priority Data

Mar. 5, 2013  (EP) .................................. 13157877

(51) Int. Cl.
*G01N 33/536* (2006.01)
*G01N 33/50* (2006.01)
(Continued)

(52) U.S. Cl.
CPC ...... *G01N 33/536* (2013.01); *B01L 3/502776* (2013.01); *C12Q 1/25* (2013.01);
(Continued)

(58) Field of Classification Search
CPC ..... B01L 2200/0694; B01L 2300/0816; B01L 2300/0883; B01L 2400/0472;
(Continued)

(56) References Cited

U.S. PATENT DOCUMENTS

| 2009/0222219 A1 | 9/2009 | Some et al. |
| 2013/0072404 A1* | 3/2013 | Miller ................... B01F 3/0807 506/11 |

(Continued)

FOREIGN PATENT DOCUMENTS

| CN | 101520414 A | 2/2009 |
| KR | 20090037670 A | 4/2009 |

(Continued)

OTHER PUBLICATIONS

Bui et al. Analytical Chemistry, vol. 83, Jan. 31, 2011, pp. 1603-1608.*

(Continued)

*Primary Examiner* — Maureen Wallenhorst
(74) *Attorney, Agent, or Firm* — Mintz Levin Cohn Ferris Glovsky and Popeo, P.C.

(57) ABSTRACT

A method for determining a biological response of a target (41, 42) to a soluble candidate substance includes the steps:
  introducing a soluble candidate substance into a laminar flow of a buffer liquid (2) to form a candidate substance solute (3) having an initial concentration profile (31);
  dispersing the initial concentration profile (31) to form a dispersed concentration profile (32);
  directing the dispersed concentration profile (32) into a detection channel (12) to form a final symmetrical concentration profile (33) therein;
  introducing a target into the detection channel (12) to obtain a combined concentration profile including a constant target concentration profile overlying the final symmetrical concentration profile (33);

(Continued)

Figure 1:
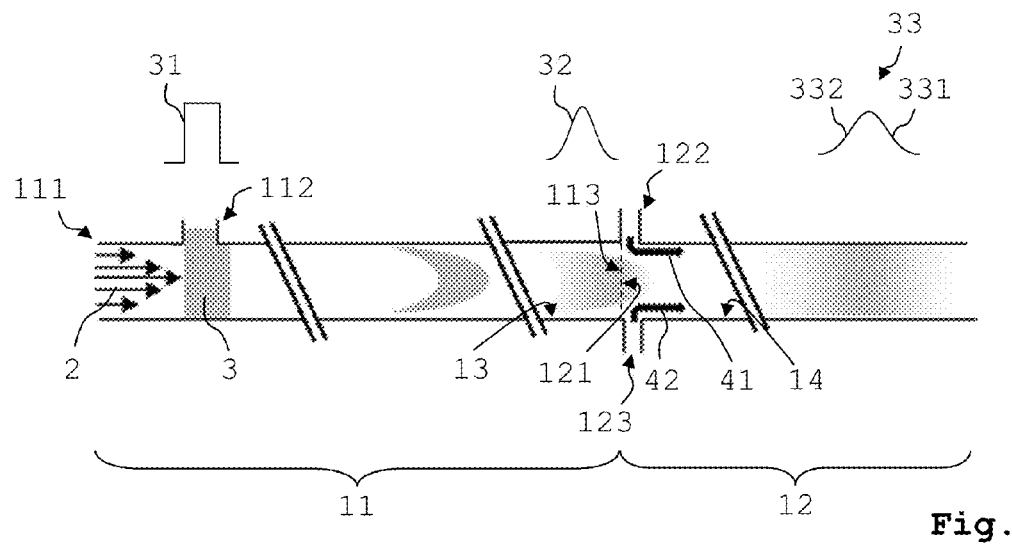

holding in the detection channel (12) at least one half of the combined concentration profile; and optically scanning the combined concentration profile to detect an optical signal representative of the biological response of the target to the soluble candidate substance.

13 Claims, 1 Drawing Sheet

(51) Int. Cl.
| | |
|---|---|
| *G01N 33/52* | (2006.01) |
| *G01N 33/558* | (2006.01) |
| *B01L 3/00* | (2006.01) |
| *C12Q 1/25* | (2006.01) |
| *G01N 21/64* | (2006.01) |

(52) U.S. Cl.
CPC ..... *G01N 21/6428* (2013.01); *G01N 21/6486* (2013.01); *G01N 33/558* (2013.01); *B01L 2200/0694* (2013.01); *B01L 2300/0816* (2013.01); *B01L 2300/0883* (2013.01); *B01L 2400/0472* (2013.01); *B01L 2400/0487* (2013.01); *G01N 2021/6439* (2013.01); *Y10T 436/2575* (2015.01); *Y10T 436/25625* (2015.01)

(58) Field of Classification Search
CPC .............. B01L 2400/0487; C12Q 1/25; G01N 2021/6439; G01N 21/6428; G01N 21/6486; G01N 33/536; G01N 33/558; Y10T 436/117497; Y10T 436/25; Y10T 436/25625; Y10T 436/2575
USPC ......... 436/52, 164, 165, 172, 174, 179, 180; 422/68.1, 81, 82.05, 82.08, 502, 503, 505; 435/4, 288.7

See application file for complete search history.

(56) References Cited

U.S. PATENT DOCUMENTS

| | | | | |
|---|---|---|---|---|
| 2013/0273564 | A1* | 10/2013 | Quinn | .................. G01N 21/272 435/7.8 |
| 2014/0080206 | A1* | 3/2014 | Dahan | ............... B01L 3/502753 435/288.7 |

FOREIGN PATENT DOCUMENTS

| | | | |
|---|---|---|---|
| WO | WO 2004/015419 | A1 | 2/2004 |
| WO | WO-2004/015419 | A1 | 2/2004 |
| WO | WO 2004/059299 | A1 | 7/2004 |
| WO | WO-2004/059299 | A1 | 7/2004 |
| WO | WO 2005/033672 | A1 | 4/2005 |
| WO | WO 2011/042509 | A2 | 4/2011 |
| WO | WO-2011/042509 | A2 | 4/2011 |

OTHER PUBLICATIONS

English Abstract for KR20090037670A, Apr. 16, 2009.
English Abstract for CN101520414A, Feb. 9, 2009.
International Search Report and Written Opinion issued in PCT/EP2014/054117 dated Apr. 28, 2014.
Long-Fei Cai et al. "Droplet-Based Microgluidic Flow Injection System with Large-Scale Concentration Gradient by a Single Nanoliter-Scale Injection for Enzyme Inhibition Assay." American Chemical Society. vol. 84. 2012 446-452.
Oliber J. Miller et al. High-Resolution Dose-Response Screening Using Droplet-Based Microfluidics. PNAS. vol. 109 No. 2. 378-383, Jan. 10, 2012.

* cited by examiner

METHOD AND SYSTEM FOR DETERMINING A BIOLOGICAL RESPONSE OF A TARGET TO A SOLUBLE CANDIDATE SUBSTANCE

RELATED APPLICATION

This application is a national stage application, filed under 35 U.S.C. §371, of International Application No. PCT/EP2014/054117 filed on Mar. 4, 2014, which claims priority to European Patent Application No. 13157877.5 filed on Mar. 5, 2013, the contents of which are hereby fully incorporated by reference.

The present invention relates to a method for determining a biological response of a target to a soluble candidate substance and to a corresponding system according to the respective independent claim.

Target-based drug discovery is by and large composed of rational drug design, chemical synthesis, biological assaying and data analysis carried out in an iterative manner until a lead structure emerges. Biological assays in order to determine potency, selectivity and efficacy of a newly synthesized drug candidate at the target of interest are a fundamental part of this workflow.

A specific type of such biological assay is a dilution assay. In principle, the dilution assay provides a candidate substance solute at different concentrations and seeks to relate the biological response of a target to different concentrations of the candidate substance solute.

WO 2011/042509 discloses a method for generating a plurality of microdroplets with different concentrations of a solute (candidate substance solute) in a solvent (buffer liquid). The microdroplets also contain a target at a constant concentration. The microdroplets are generated by introducing the soluble candidate substance into a laminar flow of the solvent flowing through a microfluidic channel to form a candidate substance solute in the solvent. Immediately after introduction into the solvent the solute has a pulse-shaped initial concentration profile. The laminar flow of buffer liquid causes the pulse-shaped initial concentration profile of the solute in the solvent to change its profile due to Taylor-Aris-dispersion into a Gaussian-shaped dispersed concentration profile.

It is to be noted in this regard, that the term "Gaussian-shaped dispersed concentration profile" as used in this application denotes a dispersed profile of concentrations which is in theory Gaussian-shaped, however, in practice the actual shape of the dispersed concentration profile may slightly deviate from the ideal Gaussian-shaped dispersed concentration profile, in particular as regards the exact symmetry of the profile. Therefore, whenever such Gaussian-shaped profile is described as being a symmetrical profile and the actual dispersed concentration profile slightly deviates from an exact Gaussian-shaped profile, the shape of the actual dispersed concentration profile may also deviate from an exactly symmetrical shape.

Turning back to the method described in WO 2011/042509, after introduction of the target into the solvent containing the Gaussian-shaped dispersed concentration profile of the solute, the continuous flow of solvent is segmented into a plurality of discrete microdroplets. These micro-droplets are generated by combining the continuous flow of the solvent containing the Gaussian-shaped dispersed concentration profile of the solute and the target at the constant concentration with an oil phase in a specific hydrodynamic flow focusing module so as to provide different mean concentrations of the solute in the individual microdroplets. The size of the steps in solute concentration is given by the difference of the mean concentration in adjacent microdroplets which relies on the droplet production rate: If the droplet production rate decreases, the size of the steps in mean concentration increases.

Several disadvantages are associated with the described method of providing target and solute in the solvent in a series of microdroplets. The microdroplets segment the concentration profile into discrete mean concentrations (the mean concentrations in the individual microdroplets). This limits the number of different mean concentrations (size of the steps in concentration) to the number of microdroplets segmenting the concentration profile, so that the "resolution" (step size) in terms of different concentrations is limited. Additionally, the use of oil to generate the microdroplets excludes lipophilic candidate substances or targets from being used because of their tendency to diffuse into the oil.

Therefore, it is an object of the invention to provide a method for determining a biological response of a target to a soluble candidate which overcomes or at least greatly reduces the disadvantages known from the prior art.

The present invention suggests a method for determining a biological response of a target to a soluble candidate substance, and comprises the following steps:

introducing a soluble candidate substance into a laminar flow of a buffer liquid flowing through a dispersion channel to form a candidate substance solute in the buffer liquid having an initial concentration profile;

by the laminar flow of the buffer liquid through the dispersion channel dispersing the initial concentration profile of the candidate substance solute in the buffer liquid to form a dispersed concentration profile of the candidate substance solute in the buffer liquid;

directing the laminar flow of the buffer liquid containing the candidate substance solute having the dispersed concentration profile into a detection channel to form a final symmetrical concentration profile of the candidate substance solute in the buffer liquid in the detection channel;

introducing a target into the detection channel in a manner so as to obtain a combined concentration profile in the buffer liquid, the combined concentration profile comprising a constant target concentration profile overlying the final symmetrical concentration profile of the candidate substance solute;

holding in the detection channel at least one half of the combined concentration profile contained in the buffer liquid; and optically scanning the at least one half of the combined concentration profile contained in the buffer liquid held in the detection channel to detect at the various concentrations of the candidate substance solute of the combined concentration profile an optical signal which is representative of the biological response of the target to the soluble candidate substance.

Accordingly, the method according to the invention suggests that at least one half of the combined concentration profile be held as a stationary continuous profile in the detection channel, so that in principle an unlimited number of detection locations can be chosen along the profile for optically scanning (limited by the resolution of the optical scanner only). The stationary continuous profile allows for optically scanning the combined concentration profile within a predetermined period of time in which the combined concentration profile is stable due to (molecular) diffusion processes being negligible during that predetermined period of time. The combined concentration profile of the candidate solute is provided in the buffer liquid only (no oil phase), so that also lipophilic candidate substances or targets can be used in the assay.

The described method is in principle applicable to known dilution assays, in which typically potency, selectivity or efficacy of a soluble candidate substance is determined at a target of interest. The "biological response of the target to the soluble candidate substance" within the meaning of the present invention includes any biological, biochemical, pharmaceutical, etc. response suitable to establish a dose-response curve by use of a dilution assay. The following exemplary tables of assay examples are classified with respect to different readouts which are representative of a biological response of the target to the soluble candidate substance.

Fluorescence

| Readout | Assay example(s) | Biological response example(s) |
| --- | --- | --- |
| Fluorescence Intensity | Fluorescence quench assays | Enzyme activity |
|  | Fluorigenic assays | Enzyme activity |
|  | Thermal shift assay | Receptor-ligand interaction |
| Time-Resolved Fluorescence (TRF) | LANCE ™ (Perkin Elmer) | Enzyme activity |
| Fluorescence Polarization | Ligand-binding assay | Receptor-ligand interaction |
|  | IMAP ™ (Mol. Devices) | Enzyme activity |
| Fluorescence Resonance Energy Transfer (FRET) | Protease assays | Enzyme activity |
| Fluorescence Correlation Spectroscopy (FCS) | Ligand-binding assay | Receptor-ligand interaction |

Luminescence

| Readout | Assay example(s) | Biological response example(s) |
| --- | --- | --- |
| Chemiluminescence | Alpha-Screen ™ (Perkin Elmer) | Enzyme activity Protein-Protein interaction |
| Bioluminescence | BRET ™ (Perkin Elmer) | Protein-Protein interactions |

Other Readouts

| Readout | Assay example(s) | Biological response example(s) |
| --- | --- | --- |
| Absorbance | Chromogenic assay | Enzyme activity |
| Raman spectroscopy | SERS Assay | Enzyme activity |

By way of example, a target may belong to the group consisting of proteins (soluble proteins, membrane proteins), such as enzymes (e.g. kinases, proteases, peptidases), transport proteins (e.g. ion channels, albumins), G-protein-coupled-receptors (e.g. histamine receptor, serotonin receptor), transcription factors, etc.

A soluble candidate substance can be understood as being a substance to which a target of interest may respond. For instance, the soluble candidate substance may be an active ingredient which is soluble per se in the buffer liquid or, alternatively, the soluble candidate substance may be an active ingredient (e.g. a pharmaceutically active substance) already solved in a solvent (e.g. a solution containing the active ingredient) and the solution containing the active ingredient is soluble in the buffer liquid. The term "soluble" refers to the capability of the definitive soluble candidate substance to solve in the respective buffer liquid used for a specific assay. The term "buffer liquid" refers to any suitable known liquid which is typically inert with respect to the biological response to be determined. The term "target" as used in this application is to be understood to comprise single substances as well as "combined targets" as described hereinafter.

The buffer liquid may be held in the detection channel by any suitable measure resulting in that the laminar flow of buffer liquid is stopped, so as to discontinue the dispersing effects in the detection channel associated with Taylor-Aris-dispersion. For the period of time needed to perform the optical scan, other (molecular) diffusion processes may be neglected but rather the combined symmetrical concentration profile contained in the buffer liquid stationarily held in the detection channel can be regarded as being stable.

Both the dispersion channel and the detection channel may be microfluidic channels having an inner diameter smaller than 2 mm, more preferably smaller than 1 mm, most preferably smaller than 100 µm. Both, the dispersion channel and the detection channel need to allow for a laminar flow of buffer liquid therethrough which requires an appropriate Reynolds number. The laminar flow of the buffer liquid causes the initial concentration profile of the candidate substance solute to change due to Taylor-Aris-dispersion (see description above). Taylor-Aris-Dispersion causes the concentration profile of the candidate substance solute to change into a Gaussian-shaped concentration profile.

In one aspect of the method according to the invention, the step of holding in the detection channel the at least one half of the combined concentration profile contained in the buffer liquid is carried out by stopping a further introduction of buffer liquid into the dispersion channel and of target into the detection channel. In a practical example, the further supply of buffer liquid is stopped by switching off a buffer liquid supply pump, so that the laminar flow of buffer liquid is discontinued. Such pump may be time-controlled so as to be automatically switched off after a predetermined period of time. This period of time starts when the laminar flow of the buffer liquid containing the dispersed concentration profile of the candidate substance solute enters the detection channel and ends when the at least one half of the combined concentration profile is entirely inside the detection channel. Similar considerations apply to stopping the introduction of target into the detection channel which can be achieved by switching off a target supply pump that introduces a laminar flow of target into the detection channel.

According to a further aspect of the method according to the invention, the laminar flow of the buffer liquid containing the candidate substance solute having the dispersed concentration profile is directed into the detection channel at a constant flow rate. Also, the target is introduced into the detection channel at a constant flow rate to obtain the combined concentration profile comprising the constant target concentration profile overlying the final symmetrical concentration profile of the candidate substance solute in the buffer liquid. This is a practical approach that allows for achieving in the detection channel a very uniform overly of the constant target concentration profile over the final concentration profile of the candidate substance solute in the buffer liquid. From a practical point of view, the introduction of the target at a constant flow rate already starts at a point of time before the final dispersed concentration profile of the candidate substance solute in the buffer liquid reaches the detection channel, so that a laminar flow of target is established at the time the final dispersed concentration profile of the candidate solute in the buffer liquid reaches the detection channel. This laminar flow of target then smoothly overlies the final dispersed concentration profile of the candidate substance solute to form the combined concentration profile in the detection channel.

According to a further aspect of the method according to the invention, the step of holding in the detection channel at least one half of the combined concentration profile contained in the buffer liquid comprises holding only one half of the combined concentration profile in the detection channel. And while generally the entire combined concentration profile or more than one half of the combined concentration profile can be held in the detection channel and scanned, it is only necessary to hold one half of the combined concentration profile in the detection channel, since all concentrations of interest are contained in one half of the combined concentration profile. Thus, the length of the detection channel can be reduced, and also the time for scanning the combined concentration profile in the detection channel (at a given resolution) can be reduced since only one half of the combined concentration profile must be optically scanned rather than the entire combined concentration profile. This may be of importance in particular in view of the very high number of assays to be performed during early stage drug discovery which should be automated to an as large extent as possible.

According to a still further aspect of the method according to the invention, the only one half of the combined concentration profile contains at least five (preferably five to six) orders of magnitude of the concentration of the candidate substance solute in the buffer liquid. Five orders of magnitude cover for example a range of 1 to 100,000 nM [nano Molar], six orders of magnitude a range of 1 to 1,000,000 nM concentrations of the candidate substance solute in the buffer liquid. This proves to be sufficient to detect (if present) any significant biological responses in the only one half of the combined symmetrical concentration profile.

According to a further aspect of the method according to the invention, the step of optically scanning in the detection channel the at least one half of the combined concentration profile contained in the buffer liquid is carried out by moving the detection channel relative to a stationarily arranged optical detection unit. Generally, only a relative movement of the at least one half of the combined concentration profile contained in the buffer liquid in the detection channel and the optical detection unit is required in order to scan the at least one half of the combined concentration profile to obtain a signal representative of the biological response of the target to the soluble candidate substance. However, since high resolution optical systems are typically very sensitive to any changes it is preferred to stationarily arrange the optical detection unit while moving the detection channel (e.g. a chip comprising the detection channel) relative to the optical detection unit.

According to a further aspect of the method according to the invention, the step of optically scanning in the detection channel the at least one half of the combined concentration profile contained in the buffer liquid is carried out by repeatedly moving the detection channel over the same range of relative positions of the detection channel and the optical detection unit, and wherein the respective signals representative of the various biological responses are then processed to form an average signal or a time-dependent signal change representative of the biological response of the target to the soluble candidate substance. Obtaining a plurality of individual signals for each concentration of the combined concentration profile and averaging the signals these signals results in a signal which is even better representative of the biological response.

According to yet a further aspect of the method according to the invention, the step of optically scanning in the detection channel the at least one half of the combined concentration profile contained in the buffer liquid is carried out at different detection sensitivities by adjusting the detection sensitivity of the optical detection unit to the optical signal which is representative of the biological response of the target to the soluble candidate and/or to an optical signal representative of the concentration of the soluble candidate substance.

In principle, any optical readout device can be employed as optical detection unit to read out the respective characteristic optical signal. For example, the optical detection unit may be a CCD camera which is typically sensitive to a light intensity corresponding to 2-3 orders of magnitude of the concentration of the candidate substance solute whereas the range of concentrations to be scanned typically spans 5-6 orders of magnitude of the concentration of the candidate substance solute. Therefore, a change in detection sensitivity is advantageous to be able to use the same CCD camera to scan the combined concentration profile over the entire range where a signal representative of the biological response of the target can be expected.

According to yet a further aspect of the method according to the invention, the target introduced into the detection channel is a combined target comprising at least two components which are separately introduced into the detection channel. For example, in case the candidate substance is a substance which is to be tested for its potency to inhibit the converting activity of an enzyme, the combined target does not only comprise the enzyme but also comprises the component converted by the enzyme without the inhibitor being present. Accordingly, the combined target comprises two components. Here, the biological response would be the activity of one component (the converting enzyme) of the combined target to convert the other component of the combined target. Both components of the combined target can be introduced separately into the detection channel so as to generate the combined concentration profile in the detection channel. This embodiment can be used, for example, to determine a half maximum inhibitory concentration ($IC_{50}$) to measure the potency of a candidate substance in inhibiting the converting activity of the enzyme.

According to a further aspect of the method according to the invention, either the soluble candidate substance forming the candidate substance solute or the target or both comprise a fluorescent marker, the fluorescent marker being capable of emitting an optically detectable fluorescent signal. In case the fluorescent marker is attached to the candidate substance (e.g. in case the concentration gradient cannot be easily detected otherwise) the optically detectable fluorescent signal emitted by the fluorescent marker allows for detecting in the detection channel the actual concentration of the candidate substance solute over the at least one half of the combined concentration profile in the buffer liquid, so that it is possible to determine in the detection channel the location of the individual concentrations over the at least one half of the combined concentration profile in the buffer liquid. A calibration (ex situ in another experiment, or in situ in the same experiment) can thus be performed. In case the target comprises a fluorescent marker, after calibration the intensity of the signal emitted by the fluorescent marker may be used as the optical signal representative of the biological response of the target to the soluble candidate. For example, in case the component to be converted by the enzyme comprises the fluorescent marker conversion of the component by the enzyme may decrease the fluorescent light from the substrate. In case both the candidate substance solute and the target comprise a fluorescent marker, it is evident that the fluorescent light of the marker of the candidate substance solute and the fluorescent light of the marker of the target must have a different wavelength so that it is possible to distinguish between fluorescent light emitted by the marker of the candidate substance solute and fluorescent light emitted by marker of the target.

Another aspect of the present invention relates to a system for determining a biological response of a target to a soluble candidate substance. The system comprises:

a dispersion channel, the dispersion channel having
  a first dispersion channel inlet for introducing a buffer liquid into the dispersion channel,
  a second dispersion channel inlet arranged downstream of the first dispersion channel inlet, for introducing a soluble candidate substance into the buffer liquid flowing through the dispersion channel to form a candidate substance solute in the buffer liquid, and
  a dispersion channel outlet arranged downstream of the first and second dispersion channel inlets, for allowing the buffer liquid containing the candidate substance solute to exit the dispersion channel,
a pump for generating a laminar flow of buffer liquid through the dispersion channel,
a candidate substance injector for introducing the soluble candidate substance into the laminar flow of buffer liquid through the dispersion channel to form the candidate substance solute in the buffer liquid having an initial concentration profile which is then dispersed by the laminar flow of the buffer liquid through the dispersion channel to form a dispersed concentration profile of the candidate substance solute in the buffer liquid,
a detection channel, the detection channel having
  a first detection channel inlet which is arranged in fluid communication with the dispersion channel outlet such that the laminar flow of the buffer liquid exiting the dispersion channel through the dispersion channel outlet and containing the dispersed concentration profile of the candidate substance solute is directed through the first detection channel inlet into the detection channel to form a final symmetrical concentration profile of the candidate substance solute in the buffer liquid in the detection channel, and
  at least one further detection channel inlet for introducing a target into the detection channel,
at least one target injector for introducing a target into the detection channel through the at least one further detection channel inlet in a manner so as to obtain a combined concentration profile comprising a constant target concentration profile overlying the final symmetrical concentration profile of the candidate substance solute in the buffer liquid,
means for holding in the detection channel at least one half of the combined concentration profile contained in the buffer liquid, and
an optical detection unit capable of and arranged to optically scan the at least one half of the combined concentration profile contained in the buffer liquid in the detection channel to detect at the various concentrations of the candidate substance solute of the combined concentration profile an optical signal representative of the biological response of the target to the soluble candidate substance, wherein the dispersion channel outlet and the first detection channel inlet are connected to each other in a manner maintaining the laminar flow at the connection of these channels and in the detection channel.

According to a further aspect of the system according to the invention, an inner wall of the dispersion channel at the dispersion channel outlet and an inner wall of the detection channel at the first detection channel inlet are of the same shape and size to provide a continuous inner channel wall contour at the connection of the dispersion channel and the detection channel.

According to yet a further aspect of the system according to the invention, the inner wall of the dispersion channel at the dispersion channel outlet and the inner wall of the detection channel at the detection channel inlet are integrally formed so as to form a common continuous inner wall.

Figure 2:
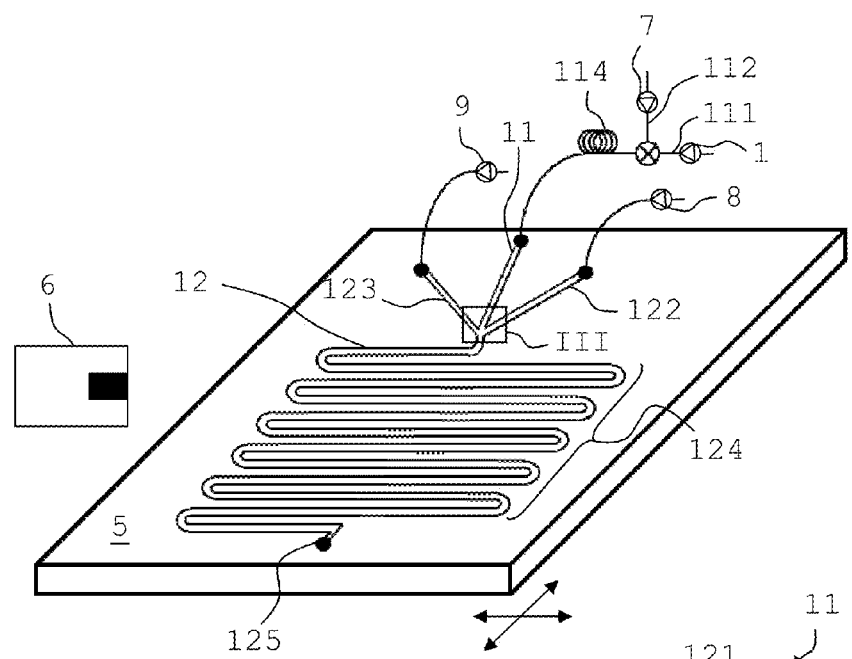
Figure 3:
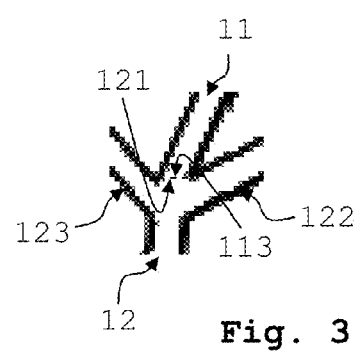

Further advantageous aspects of the invention become apparent from the following description of the invention with reference to the accompanying drawings in which:

FIG. 1 shows a sectional view of a dispersion channel and a detection channel which are integrally formed during carrying out the method according to the invention; and FIG. 2 shows a perspective view of an embodiment of a system according to the invention in which a detection channel is arranged on a chip which is movable relative to an optical detection unit, and FIG. 3 shows an enlarged view of detail III of FIG. 2.

FIG. 1 shows a dispersion channel 11 and a detection channel 12 which are integrally formed. Dispersion channel 11 has a first dispersion channel inlet 111, a second dispersion channel inlet 112, and a dispersion channel outlet 113. Second dispersion channel inlet 112 is arranged downstream of first dispersion channel inlet 111, and dispersion channel outlet 113 is arranged downstream of first and second dispersion channel inlets 111, 112. Detection channel 12 has a detection channel inlet 121 which is identical with dispersion channel outlet 113, and two further detection channel inlets 122, 123.

In use, a buffer liquid 2 is introduced into dispersion channel 11 through first dispersion channel inlet 111 with the aid of a pump 1 (see FIG. 2), and the parabolic velocity profile of the laminar flow of buffer liquid 2 flowing through dispersion channel 11 is indicated by the arrows. A candidate substance injector 7 is arranged at second dispersion channel inlet 112 to introduce a soluble candidate substance into the laminar flow of buffer liquid 2 flowing through dispersion channel 11. In the embodiment shown, the soluble candidate substance is a soluble candidate substance capable of inhibiting the activity of a converting enzyme. Immediately after introduction into the laminar flow of buffer liquid, the soluble candidate substance solves in the buffer liquid 2 to form a candidate substance solute 3 in the buffer liquid 2 having an initial concentration profile schematically indicated by the rectangular profile 31 depicted above second dispersion channel inlet, although the actual initial concentration profile is not rectangular as shown.

As has already been described above, the initial concentration profile 31 is then dispersed by Taylor-Aris-dispersion caused by the laminar flow of buffer liquid 2 through the dispersion channel 11 so that the initial concentration profile 31 changes into a dispersed concentration profile indicated by Gaussian curve 32 depicted above the outlet 113 of dispersion channel 11. Buffer liquid 2 containing the dispersed concentration profile 32 is then directed into detection channel 12 through the inlet 121 of detection channel 12 which in the embodiment shown is identical with the outlet 113 of dispersion channel 11, since dispersion channel 11 and detection channel 12 are integrally formed so that the inner wall 13 of dispersion channel 11 at dispersion channel outlet 113 and the inner wall 14 of detection channel 12 at detection channel inlet 121 are of the same size and shape to provide for a continuous inner channel wall at the connection of dispersion channel 11 and detection channel 12. This allows transferring the buffer liquid 2 out of dispersion channel 11 and into detection channel 12 while maintaining the laminar flow so that dispersed concentration profile 32 is further dispersed in the detection channel 12 to form a final symmetrical concentration profile represented by Gaussian curve 33 depicted above detection channel 12.

Detection channel 12 comprises two further detection channel inlets 122, 123 which are arranged at the connection of dispersion channel 11 to detection channel 12. Two target components 41, 42 are separately introduced through the two further detection channel inlets 122, 123 with the aid of two target injectors 8, 9 (see FIG. 2). In practice, the flow of buffer liquid 2 as well as the flows of the combined target comprising the two target components 41, 42 (e.g. two separate liquid target solutions) are continuously supplied before the soluble candidate substance is introduced into dispersion channel 11. This provides for a constant concentration of the combined target comprising the two components 41, 42 in detection channel 12. This constant profile of the combined target overlies the final symmetrical concentration profile 33 of the candidate substance solute 3 in the detection channel 12 to form a combined concentration profile comprising the constant target concentration profile overlying the final symmetrical concentration profile 33 of the candidate substance solute.

As has already been discussed further above, introducing a combined target comprising two components 41, 42 allows for carrying out specific biological assays with combined targets. Such a combined target may comprise, for example, an enzyme 41 and a component 42 to be converted by the enzyme. The enzymatic activity as the biological response can be determined by detecting the conversion rate of component 42. If the candidate substance is an enzyme inhibitor inhibiting the conversion activity of enzyme 41, a decrease in enzyme activity would have to be the biological response.

Once at least one half of the combined concentration profile comprising the constant target concentration profile overlying the final symmetrical concentration profile 33 of the candidate substance solute 3 has entered into detection channel 12, it is held in detection channel. As has already been explained above, one half of the combined concentration profile is sufficient due to the symmetry of the combined concentration profile. Of course, it is possible to hold the entire combined concentration profile in the detection channel 12. Holding the buffer liquid 2 containing the at least one half of the combined concentration profile in the detection channel is achieved by stopping further supply of buffer liquid 12 and also of target components 41, 42 into detection channel 12. By stopping the laminar flow, Taylor-Aris-Dispersion is discontinued, while other (molecular) diffusion processes can be neglected within the period of time necessary to carry out the step of optically scanning the at least one half of the combined concentration profile held in the detection channel. The biological response may be detected in the present example by optically detecting a fluorescent signal emitted by a fluorescent marker comprised by the component 42. Conversion of the component 42 by the enzyme results in a decrease in intensity of the detected fluorescent signal (an increase may be detected in assays based on quenching effects). This decrease in the detected fluorescent signal is a consequence of the enzyme activity. Accordingly, if the candidate substance is an enzyme inhibitor inhibiting the enzyme to convert the component 42, the detected fluorescent signal from the component 42 would either not decrease at all or only decrease to a lesser extent. Accordingly, in this example the optically detected signal representative of the biological response is the change in intensity of the fluorescent light emitted by the fluorescent marker comprised by the component 42.

This reduced decrease in intensity can be determined over the at least one half of the combined concentration profile held in the detection channel 12. Since the at least one half of the combined concentration profile comprises continuous "dilutions" over the at least one half of the combined concentration profile (different concentrations of the candidate substance solute 3 in the buffer liquid spanning ideally the entire range of concentrations between zero and the initial concentration, however, at least about five to six orders of magnitude), the dilution assay allows for determining the biological response over the entire range at practically all concentrations of the candidate substance solute 3 contained in the combined concentration profile.

The fluorescent light may be detected along the channel by means of a CCD camera 6 (see FIG. 2) as an optical detection unit. The CCD camera detects the intensity of the fluorescent light at different detection locations of the detection channel 12 relative to the CCD camera 6.

An embodiment of the system according to the invention is shown in FIG. 2. The system may be used for example, to carry out the method described above in connection with FIG. 1. In this embodiment of the system according to the invention, a portion of the dispersion channel 11 and detection channel 12 are arranged on a chip 5. Chip 5 is movably arranged to allow for changing the position of various portions of the detection channel 12 relative to the CCD camera 6 as optical detection unit. Only a portion of dispersion channel 11 is arranged on chip 5 while dispersion channel 11 also comprises a capillary 114 to extend the length of dispersion channel to provide for sufficient dispersion of the initial concentration profile 31 due to Taylor-Aris-dispersion. Pump is arranged at dispersion channel inlet 111 for pumping buffer liquid into dispersion channel 11 and to cause a laminar flow therethrough. Second dispersion channel inlet 112 is arranged downstream of first dispersion channel inlet 111 where the soluble candidate substance is introduced into the buffer liquid with the aid of candidate substance injector 7. With the aid of pump 1, a laminar flow is generated both through capillary 114 and the on-chip portion of dispersion channel 11, as has been explained above, dispersing the initial profile of the candidate substance solute represented by rectangular curve 31 by Taylor-Aris-dispersion into the dispersed profile represented by Gaussian curve 32 (see FIG. 1). Dispersion channel outlet 113 as well as the two further detection channel inlets 122, 123 are arranged on chip 5. The two further detection channel inlets 122, 123 merge with first detection channel inlet 121 which is identical to dispersion channel outlet 113 (see FIG. 3). Detection channel 12 comprises a meander-shaped portion 124 arranged on chip 5. A detection channel outlet 125 is arranged at the end of detection channel 12 for draining the buffer liquid from detection channel 12.

Embodiments of the invention have been described with the aid of the drawings. However, various modifications and changes to the described embodiments are possible without departing from the general teaching underlying the present invention. Therefore, the invention is not to be understood as being limited to the described embodiments, but rather the scope of protection is defined by the appended claims.

The invention claimed is:

1. A method for determining a biological response of a target to a soluble candidate substance, the method comprising the following steps:
    introducing a soluble candidate substance into a laminar flow of a buffer liquid flowing through a dispersion channel to form a candidate substance solute in the buffer liquid having an initial concentration profile;
    by the laminar flow of the buffer liquid through the dispersion channel dispersing the initial concentration profile of the candidate substance solute in the buffer liquid to form a dispersed concentration profile of the candidate substance solute in the buffer liquid;
    directing the laminar flow of the buffer liquid containing the candidate substance solute having the dispersed concentration profile into a detection channel to form a final symmetrical concentration profile of the candidate substance solute in the buffer liquid in the detection channel;
    introducing a target into the detection channel in a manner so as to obtain a combined concentration profile in the buffer liquid, the combined concentration profile comprising a constant target concentration profile overlying the final symmetrical concentration profile of the candidate substance solute;
    holding in the detection channel at least one half of the combined concentration profile contained in the buffer liquid; and
    optically scanning the at least one half of the combined concentration profile contained in the buffer liquid held in the detection channel to detect at the various concentrations of the candidate substance solute of the combined concentration profile an optical signal which is representative of the biological response of the target to the soluble candidate substance.

2. A method according to claim 1, wherein the step of holding in the detection channel the at least one half of the combined concentration profile contained in the buffer liquid is carried out by stopping a further introduction of buffer liquid into the dispersion channel and of target into the detection channel.

3. A method according to claim 1, wherein the laminar flow of the buffer liquid containing the candidate substance solute having the dispersed concentration profile is directed into the detection channel at a constant flow rate, and wherein the target is introduced into the detection channel at a constant flow rate to obtain the combined concentration profile comprising the constant target concentration profile overlying the final symmetrical concentration profile of the candidate substance solute in the buffer liquid.

4. A method according to claim 1, wherein the step of holding in the detection channel at least one half of the combined concentration profile contained in the buffer liquid comprises holding only one half of the combined concentration profile in the detection channel.

5. A method according to claim 4, wherein the only one half of the combined concentration profile contains at least five orders of magnitude of the concentration of the candidate substance solute in the buffer liquid.

6. A method according to claim 1, wherein the step of optically scanning in the detection channel the at least one half of the combined concentration profile contained in the buffer liquid is carried out by moving the detection channel relative to a stationarily arranged optical detection unit.

7. A method according to claim 6, wherein the step of optically scanning in the detection channel the at least one half of the combined concentration profile contained in the buffer liquid is carried out by repeatedly moving the detection channel over the same range of relative positions of the detection channel and the optical detection unit, and wherein the respective signals representative of the various biological responses are then processed to form an average signal or a time-dependent signal change representative of the biological response of the target to the soluble candidate substance.

8. A method according to claim 6, wherein the step of optically scanning in the detection channel the at least one half of the combined concentration profile contained in the buffer liquid is carried out at different detection sensitivities by adjusting the detection sensitivity of the optical detection unit to the optical signal which is representative of the biological response of the target to the soluble candidate substance and/or to an optical signal representative of the concentration of the soluble candidate substance.

9. A method according to claim 1, wherein the target introduced into the detection channel is a combined target comprising at least two components which are separately introduced into the detection channel.

10. A method according to claim 1, wherein either the soluble candidate substance forming the candidate substance solute or the target or both comprise a fluorescent marker, the fluorescent marker being capable of emitting an optically detectable fluorescent signal.

11. A system for determining a biological response of a target to a soluble candidate substance, the system comprising:
    a dispersion channel, the dispersion channel having a first dispersion channel inlet for introducing a buffer liquid into the dispersion channel, a second dispersion channel inlet arranged downstream of the first dispersion channel inlet for introducing a soluble candidate substance into the buffer liquid flowing through the dispersion channel to form a candidate substance solute in the buffer liquid, and a dispersion channel outlet arranged downstream of the first and second dispersion channel inlets for allowing the buffer liquid containing the candidate substance solute to exit the dispersion channel;
    a pump for generating a laminar flow of buffer liquid through the dispersion channel;
    a candidate substance injector for introducing the soluble candidate substance into the laminar flow of buffer liquid through the dispersion channel to form the candidate substance solute in the buffer liquid having an initial concentration profile which is then dispersed by the laminar flow of the buffer liquid through the dispersion channel to form a dispersed concentration profile of the candidate substance solute in the buffer liquid;
    a detection channel, the detection channel having a first detection channel inlet which is arranged in fluid communication with the dispersion channel outlet such that the laminar flow of the buffer liquid exiting the dispersion channel through the dispersion channel outlet and containing the dispersed concentration profile of the candidate substance solute is directed through the first detection channel inlet into the detection channel to form a final symmetrical concentration profile of the candidate substance solute in the buffer liquid in the detection channel, and at least one further detection channel inlet for introducing a target into the detection channel;

at least one target injector for introducing a target into the detection channel through the at least one further detection channel inlet in a manner so as to obtain a combined concentration profile comprising a constant target concentration profile overlying the final symmetrical concentration profile of the candidate substance solute in the buffer liquid;

means for holding in the detection channel at least one half of the combined concentration profile contained in the buffer liquid; and an optical detection unit capable of and arranged to optically scan the at least one half of the combined concentration profile contained in the buffer liquid in the detection channel to detect at the various concentrations of the candidate substance solute of the combined concentration profile an optical signal representative of the biological response of the target to the soluble candidate substance, wherein the dispersion channel outlet and the first detection channel inlet are connected to each other in a manner maintaining the laminar flow at the connection of these channels and in the detection channel.

12. A system according to claim 11, wherein an inner wall of the dispersion channel at the dispersion channel outlet and an inner wall of the detection channel at the first detection channel inlet are of the same shape and size to provide a continuous inner channel wall contour at the connection of the dispersion channel and the detection channel.

13. A system according to claim 12, wherein the inner wall of the dispersion channel at the dispersion channel outlet and the inner wall of the detection channel at the detection channel inlet are integrally formed so as to form a common continuous inner wall.

\* \* \* \* \*